United States Patent
Barberousse et al.

(10) Patent No.: US 6,291,433 B1
(45) Date of Patent: Sep. 18, 2001

(54) DERIVATIVES OF α-D-THIOXYLOSIDE AND THEIR USE AGAINST ATHEROMA

(75) Inventors: Veronique Barberousse, Hauteville-les-Dijon; Christiane Legendre, Velars-sur-Ouche; Soth Samreth, Daix; Alan Dunlap Edgar, Saint-Julien, all of (FR)

(73) Assignee: Fournier Industrie et Sante, Paris (FR)

( * ) Notice: Subject to any disclaimer, the term of this patent is extended or adjusted under 35 U.S.C. 154(b) by 0 days.

(21) Appl. No.: 09/486,226

(22) PCT Filed: Jul. 7, 1999

(86) PCT No.: PCT/FR99/01387

§ 371 Date: Feb. 24, 2000

§ 102(e) Date: Feb. 24, 2000

(87) PCT Pub. No.: WO99/67261

PCT Pub. Date: Dec. 29, 1999

(51) Int. Cl.[7] .................. A61K 31/7034; C07H 15/20
(52) U.S. Cl. .................. 514/24; 514/25; 536/4.1
(58) Field of Search ............... 536/4.1; 514/24, 514/25

(56) References Cited

U.S. PATENT DOCUMENTS

| | | | |
|---|---|---|---|
| 4,432,973 | 2/1984 | Picart | 424/180 |
| 4,598,068 | 7/1986 | Samreth et al. | 514/25 |
| 4,877,808 | 10/1989 | Samreth et al. | 514/432 |
| 5,101,048 | 3/1992 | Bajgrowicz et al. | 549/28 |

FOREIGN PATENT DOCUMENTS

| | | |
|---|---|---|
| 0 051 023 | 5/1982 | (EP) . |
| 0 133 103 | 2/1985 | (EP) . |
| 0 290 321 | 11/1988 | (EP) . |
| 0 365 397 | 4/1990 | (EP) . |

OTHER PUBLICATIONS

Bellamy et al., "Glycosylated Derivatives of Benzophenone, Benzhydrol, and Benzhydril as Potential Venous Antithrombotic Agents", *J. Med. Chem.*, vol. 36, 1993, pp. 898–903.

Lugemwa et al., "Estradiol β–D–Xyloside, an Efficient Primer for Heparan Sulfate Biosynthesis", *Journal of Biological Chemistry*, vol. 266, No. 11, Apr. 15, 1991, pp. 6674–6677.

Paigen et al., "Atherosclerosis Susceptibility Differences among Progenitors of Recombinant Inbred Strains of Mice", *Arteriosclerosis*, vol. 10, 1990, pp. 316–323.

Masson et al., "The Effect of the β–D–Xyloside Naroparcil on Circulating Plasma Glycosaminoglycans", Journal of Biological Chemistry, vol. 270, No. 6, pp. 2662–2668 (1995).

*Primary Examiner*—Gary Geist
*Assistant Examiner*—Leigh C. Maier
(74) *Attorney, Agent, or Firm*—Crowell & Moring LLP

(57) ABSTRACT

The present invention concerns, as new industrial products, the α-D-xylose compounds of formula I:

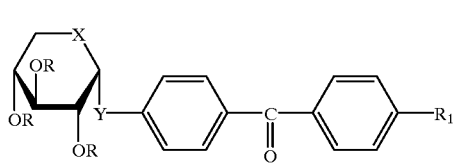

wherein
X and Y represent, independently of one another, an oxygen atom or a sulphur atom,
$R_1$ represents a CN, $CF_3$ or $SO_2CH_3$ group, and
R represents a hydrogen atom or an aliphatic acyl group containing 2 to 5 carbon atoms.

It also concerns a method for the preparation and the use in therapeutics of said compounds of the formula I.

9 Claims, No Drawings

DERIVATIVES OF α-D-THIOXYLOSIDE AND THEIR USE AGAINST ATHEROMA

CROSS-REFERENCE TO RELATED APPLICATION

This application claims the benefit of priority of Provisional Application Ser. No. 60/090,566, filed Jun. 24, 1998.

BACKGROUND OF THE INVENTION

The present invention concerns, as new industrial products, the derivatives of α-D-xylose defined by formula I below. It also concerns the process for the preparation of these compounds, as well as the therapeutic compositions containing them as active ingredients.

Derivatives of β-D-xyose, in particular derivatives of benzoyl- or α-hydroxy-benzyl-phenyl β-xylosides, recommended in therapeutics for the treatment of venous thromboses, are already known, for example, according to EP-A0051023.

Derivatives of benzyl-phenyl β-D-xylosides, exhibiting a hypocholesterolemiant and/or hypolipidemiant activity, are also known according to EP-A-0133103.

Derivatives of the type β-D-phenylthioxylosides, used for their antithrombotic activity, are also known according to EP-A0365397, EP-A-0290321, EP-A-0133103 and EP-A-0051023.

The antithrombotic activity of a certain number of derivatives of β-xylose has also been reported and studied in the article of J. Med. Chem, 1993, 36, (no. 7) pages 898903. Research carried out in the laboratory has shown that these derivatives of β-D-xylose are good substrates of galactosyl transferase I. For this reason, these compounds, active when taken orally, initiate the synthesis of glycosaminoglycanes (GAGs). After administration of the compounds orally, the circulation rates of GAGs are appreciably increased and approximately 20% of the latter display an activity of the dermatan-sulphate type capable of inhibiting thrombin, via HC II (Heparin Cofactor II), this initiation of the biosynthesis of GAGs probably being responsible for the antithrombotic activity observed experimentally for the compounds mentioned previously. In correlation with the potential of these compounds to reduce the formation of venous thromboses, only the β configuration derivatives of D-xylose increase the synthesis of GAGs. The other derivatives of the glycopyranoside type have proved to be inactive in this area, both from the biological standpoint on the synthesis of GAGs, as well as from the pharmacological standpoint on the reduction or prevention of venous thromboses.

The activity of certain derivatives of β-D-xylose, in particular estradiol β-D-xyloside, has been studied in the publication Journal of Biological Chemistry, 1991, 266, (No. 11) pages 6674–6677 and the authors establish a relationship between this compound and the biosynthesis of heparane sulphate, as well as an inflator role of β-D-xyloside in the synthesis of chondroitin sulphate. These studies confirm the benefit of derivatives of β-D-xylose for the treatment or the prevention of venous thromboses.

According to the invention, it is proposed to provide a new technical solution making it possible to arrive at new products that are biologically beneficial with respect to arterial atheromatous platelets.

SUMMARY OF THE INVENTION

According to the new technical solution of the invention, use is made of products of the type α-D-xylose or α-D-thioxylose.

It has in fact been found, in a surprising manner, that derivatives of D-xylose or of 5-thio-D-xylose no longer displaying the β configuration, but the a configuration on the anomeric carbon, possess a particularly beneficial activity for the prevention or the regression of arterial atheromatous platelets.

The new products according to the invention, which are compounds of α-D-xylose, are characterised in that they are selected from the compounds of the general formula I:

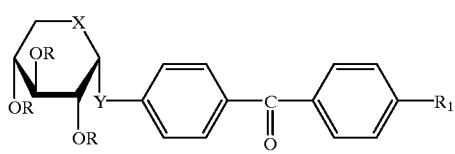

(I)

wherein

X and Y represent, independently of one another, an oxygen atom or a sulphur atom, $R_1$ represents a CN, $CF_3$ or $SO_2CH_3$ group, and R represents a hydrogen atom or an aliphatic acyl group containing 2 to 5 carbon atoms.

According to another aspect of the invention, a composition is provided that is characterised in that it contains, in association with a physiologically acceptable excipient, a therapeutically effective quantity of at least one compound of the formula I.

It is also recommended to use the compound of the formula I as an antiatheromatous drug.

DETAILED DESCRIPTION OF THE INVENTION

As presented in formula I above, the compounds according to the invention are derivatives of α-D-xylose or α-D-thioxylose, substituted on the anomeric carbon in the a position by a substituted benzophenone group.

The hydroxyl functions of D-xylose or D-thioxylose can be free or substituted by an acyl group containing 2 to 5 carbon atoms, preferably the acetyl group.

Aliphatic acyl group containing 2 to 5 carbon atoms is understood here to mean an acyl group with a straight, branched or cyclised chain, such as in particular $CH_3CO$, $CH_3CH_2CO$, $(CH_3)_2CHCO$, $(CH_3)_3CCO$, or cyclopropylcarbonyl.

The compounds of the formula I can be prepared according to a method known per se by using conventional reactive mechanisms. According to a preferred operating method, a benzophenone of the formula II is reacted (according to a coupling reaction):

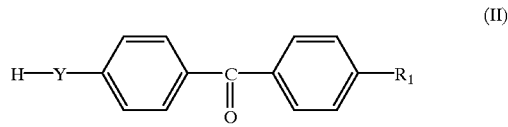

(II)

wherein Y is the oxygen atom or the sulphur atom and $R_1$ represents CN, $CF_3$ or $SO_2CH_3$, with a compound of D-ylose (or of 5-thio-D-xylose) of the formula III:

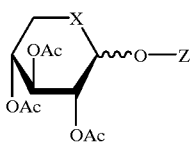

where ―w― represents a bond of indeterminate configuration (α, β or α/β mixture), X is an oxygen atom or a sulphur atom, Ac represents the acetyl group, Z represents an acetyl group or a trichloromethylimino group [—C(═NH)—CCl₃], the reaction being conducted in a solvent and in the presence of a Lewis acid, in order to obtain a compound of the formula I after purification:

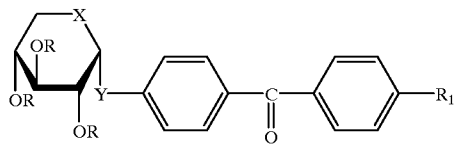

wherein
X, Y and R₁ retain the same significance as in the starting products and R represents an acetyl group.

The compounds of the formula I in which R is a hydrogen atom can be obtained from the preceding compounds, in which R is the acetyl group, by the action of a base such as for example sodium methylate or ammonia which permit the acetyl group to be replaced by a hydrogen atom.

The compounds of the formula I in which R is a $C_2$–$C_5$ acyl group, such as defined above, can be obtained from compounds with formula I in which R is a hydrogen atom, by the action of chloride or acid anhydride corresponding to the desired $C_2$–$C_5$ acyl group, in the presence of an aprotic base such as for example triethylamine or pyridine, and in a solvent such as for example dichloromethane.

Briefly, the process of preparation according to the invention comprises (a) the II+III coupling reaction and the purification of the compound I (R=Ac) thus obtained, (b) if necessary the hydrolysis (saponification) of said compound of the formula I (R=Ac) so as to obtain the deacetylated compound with formula I (R=H), and (c) if necessary the esterification of said compound of the formula I (R=H) so as to obtain any other esterified compound of the formula I (R=acyl, in particular an acyl group different from Ac).

The compounds of the formula I are useful in therapeutics as active principles of drugs intended for the treatment or prevention of atherosclerosis.

According to the invention, it is recommended to use a product selected from the group consisting of the compounds of the formula I above for the preparation of an antiatheromatous drug intended for use in therapeutics with respect to atherosclerosis.

The preferred products according to the invention, in view of the beneficial properties with respect to atherosclerosis, are the compounds of the formula I where R₁ is CN₁, and among the latter the products in which X=Y=S or X=Y=O.

The following non-limiting examples of preparation permit the advantages of the invention to be better understood and appreciated.

EXAMPLE 1

[4-(4cyanobenzoyl)phenyl]2,3,4tri-O-acetyl-1,5dithio-α-D-xylopyranoside

A suspension of 5 g (15.10⁻³ mol) of tetraacety-O-thio-D-xylopyranose, 4.3 g (18.10⁻³ mol) of 4(4mercaptobermoyl)benzonitrile and 5 g of 4 Å molecular sieve is prepared in 100 ml of acetonitrile and 4 ml of boron trifluaride etherate (at 48%, d=1.13) is added at 0° C. while stirring. The reaction mixture is allowed to return to room temperature and stirring is carried on for one hour. The mixture is then filtered, then concentrated under reduced pressure. The residue is dissolved in ethyl acetate and the solution is washed with diluted soda, then with diluted hydrochloric acid and finally with water until neutrality. The organic phase is dried and concentrated under reduced pressure. The residue is purified by chromatography on silica gel, eluting with a toluenelethyl acetate mixture (6/1; v/v). 7 g of the at sought compound is thus obtained in a mixture with the β isomer (the two isomers are in the ratio α/β=60/40). This mixture is dissolved in 15 ml of ethyl acetate and 15 ml of ethyl ether is added. The crystals obtained (essentially the β isomer) are eliminated by filtration and the filtrate is concentrated under reduced pressure. 5.4 g of the sought compound is thus obtained containing 20% of the β isomer (yield=63%). The sought compound is obtained with 98% purity in the a isomer after two recrystallisations in methanol.

F=144–146° C.

$[\alpha]^{24}_D$=+328° (c=0.42; $CH_2Cl_2$)

EXAMPLE 2

[4-(4cyanobenzoyl)phonyl]1,5-dithioa-α-xylopyranoside

A solution of 10.27 g (20.10⁻³ mol) of the compound obtained according to example 1 is prepared in 100 ml of methanol and 35 ml of tetrahydrofuran. 1.15 ml (4.10⁻³ mol) of a solution of sodium methylate is then added at 10–15° C. After 20 min. while stirring at 10–15 °C., the reaction mixture is percolated on an IR 120 resin (H⁺). The solution is decolourised by means of activated carbon, filtered and concentrated under reduced pressure. The residue is crystallised in methanol. After recrystallisation in methanol, 5 g of the sought product is obtained in the form of white crystals (yield=65%).

F=142° C.

$[\alpha]_D^{20}$ =+508° (c=0.42; $CH_3OH$)

EXAMPLE 3

[4-(4cyanobenzoyl)phenyl]2,3,4tri-O-acetyle-α-D-xylopyranoside

A mixture of 9 g (28.3.10⁻³ mol) of tetra-O-acetyl-D-xylose and 8 g (35.9·10⁻³ mol) of 4-(4-hydroxybenzoyl) benzonitrile is prepared in 90 ml of dichloromethane. 8 ml (68.4.10⁻³ mol) of tin tetrachloride is then added drop by drop at room temperature, then the reaction medium is brought to 45° C., for 15 hours, while stirring. The mixture is then poured onto ice and diluted hydrochloric acid; extraction is then performed with ethyl acetate in acid medium, then the united organic phases are washed with a diluted solution of hydrochloric acid, then with water, with a diluted soda solution, then with water. The organic phase is dried on magnesium sulphate then concentrated under reduced pressure. The raw product is purified by chromatography on silica gel, eluting with the aid of a toluene/ethyl acetate mixture (5/1; v/v). 3.3 g of the sought product is thus obtained in the form of a white powder (yield=24%).

F=75° C.

$[\alpha]_D^{26}$=+146.3° (c=0.36; $CH_3OH$)

EXAMPLE 4

[4-(4-cyanobenzoyl)phenyl]α-D-xylopyranoside 4.3 g ($8.94 \cdot 10^{-3}$ mol) of the compound obtained according to example 3 is added to 50 ml of a saturated solution of ammonia in methanol, at 0° C., and the mixture is held for 3 hours at 0° C. while stirring, then for 2 hours at room temperature. The reaction medium is then concentrated under reduced pressure and the residue is purified by chromatography on silica gel, eluting with a dichloromethane/methanol mixture (10/1; v/v). The pure fraction obtained is concentrated to eliminate the solvents, then the product is put into suspension in distilled water; the mixture is congealed and freeze-dried. 2.15 g of the sought product is thus obtained in the form of a crushed white powder (yield=67%).

F=186–187° C.

$[\alpha]^{26}_D$=+155° (c=0.40; $CH_3OH$)

EXAMPLE 5

[4-(4yanobenzoyl)phenyl]2,3,4tri-O-acetyl-1-thio-α-D-xylopyranoside

Operating in a similar manner to example 3, starting from 4-(4-mercapto-benzoyl)benzonitrile, the sought product is obtained in the form of a white solid (yield=11%).

F=158–159° C.

$[\alpha]^{26}_D$=+161° (c=0.38; $CH_2Cl_2$)

EXAMPLE 6

[4-(4-cyanobenzoyl)phenyl]1-thio-α-D-xylopyranoside

Operating in a similar manner to example 4, starting from the compound obtained according to example 5, the sought product is obtained in the form of a cream powder (yield=90%).

F=198° C.

$[\alpha^{26}_D$=+245° (c=0.30; $CH_3OH$)

EXAMPLE 7

[4-(cyanobenzoyl)phenyl]2,3,4tri-O-acetyl-5-thio-α-D-xylopyranoside)

A suspension of 2 g ($9 \cdot 10^{-3}$ mol) of 4-(4hydroxy-benzoyl)benzonitrile is prepared in 40 ml of dichloromethane, 1 g of 4 Å molecular sieve is added and the mixture is cooled to −30° C. 1.8 ml ($8 \cdot 10^{-3}$ mol) of triethylsilyl trifluoromethanesulphonate is slowly added while stirring, then a solution of 3.9 g ($9 \cdot 10^{31}{}^3$ mol) of 2,3,4-tri-O-acetyl-5-thio-α-xylopyranosyl trichloroacetimidate in 20 ml of dichloromethane. The reaction mixture is stirred for 4 hours at −30° C. then for 16 hours at 0° C. After neutralisation with the aid of a collodine solution, the reaction medium is filtered. The filtrate is diluted in 200 ml of ethyl acetate and the organic phase obtained is washed with a solution of diluted soda, then with water, with the aid of a diluted hydrochloric acid solution, then with water and dried on magnesium sulphate. After concentration of the solution under reduced pressure, the residue is purified by chromatography on silica gel, eluting with a methylcyclohexane-ethyl acetate mixture (5/2; v/v). 0.86 g of the sought product is thus obtained in the form of a beige powder (yield=19%).

F=+85° C.

$[\alpha]^{21}_D$=+365° (c=0.3; $CH_2Cl_2$)

EXAMPLE 8

[4-(4cyanobenzoyl)pheny]5-thio-α-D-xylopyranoside

Operating in a similar manner to example 4, starting from the compound obtained according to example 7, the sought product is obtained in the form of a clear beige powder (yield=73 %).

F=180° C.

$[\alpha]^{24}_D$=+476° (c=0.32; $CH_3OH$)

EXAMPLE 9

[4-[4-(trifluoromethyl)benzoy]phenyl]2,3,4tri-O-acetyl-α-D-xylopyranoside

A solution of 2.5 g ($9.4 \cdot 10^{-3}$ mol) of (4-hydroxy-phenyl)[4-(trifluoromethyl)phenyl] methanone and 3.5 g ($11 \cdot 10^{-3}$) of tetra-O-acetyl-xylose is prepared in 30 ml of acetonitrile and 1 g of 4 Å molecular sieve is added. The mixture is cooled to 0° C. and 7.2 ml ($58 \cdot 10^{-3}$ mol) of boron trifluoride etherate is added drop by drop while stirring. The reaction medium is then held at room temperature for 15 hours while stirring, then it is filtered. The filtrate is diluted with ethyl acetate and the organic phase is washed with a solution of diluted soda, with water, with a solution of diluted hydrochloric acid and again with water. After drying on magnesium sulphate, the organic phase is concentrated under reduced pressure and the residue is purified by chromatography on silica gel, eluting with the aid of a methylcyclohexane-ethyl acetate mixture (5/2; v/v). 0.46 g of the sought product is thus obtained in the form of an amorphous beige solid (yield=10%).

F=65° C.

$[\alpha]^{26}_D$=+141° (c=0.32; $CH_2Cl_2$)

EXAMPLE 10

[4-[4-(trfluoromethyl)benzoyl]pheny]α-D-xylopyranoside 0.370 g ($0.7 \cdot 10^{-3}$ mol) of the compound obtained according to example 9 is dissolved in 20 ml of methanol and 40 µl of a solution of sodium methylate at 25% in the methanol is added. The solution is held for two hours while stirring, then approx. 0.5 g of 120 IR resin is added in acidic form. After filtration, the filtrate is concentrated under reduced pressure. 240 mg of the sought product is thus obtained in the form of a beige solid (yield=85%).

F=188° C. $[\alpha]^{21}_D$=+165° (c=027; $CH_3OH$)

EXAMPLE 11

[4-[4-(trifluoromethyl)benzoyl]phenyl]2,3,4tri-O-acetyl5-thio-α-D-xylopyranoside Operating in a similar manner to example 7, starting from (4-hydroxyphenyl)[4-(trifluoromethyl)phenyl]methanone, the sought product is obtained in the form of a beige amorphous solid (yield=19.5%).

F=65° C.

$[\alpha]_D$=+320° (c=0.34; $CH_2Cl_2$)

EXAMPLE 12

[4-[4-(trifluoromethyl)benzoyl]phenyl]5-thio-α-D-xylopyranoside

Operating in a similar manner to example 10, starting from the compound obtained according to example 11, the sought product is obtained in the form of an amorphous white powder (yield=80%).

F=82° C.

$[\alpha]^{22}_D$=+378° ( c=0.25; $CH_3OH$)

PREPARATION I

Dimethylcarbamothioic acid, O-[4-4-(trifluoromethyl)benzoyl]phenyl]ester

A solution of 10 g (37.6·10$^{-3}$ mol) of (4-hydroxy-phenyl) [4-(trifluoromethyl)phenyl] methanone is prepared in 100 ml of acetone and a solution of 2.94 9 (45·10$^{-3}$ mol) of potassium hydroxide (at 80%) in 80 ml of water is slowly added while stirring and at room temperature. A solution of 5.11 g (41.3·10$^{-3}$ mol) of dimethylthiocarbamoyl chloride in 70 ml of acetone is then added. The reaction mixture is held at room temperature for 8 hours while stirring, then concentrated at reduced pressure. The raw product is put into suspension in 60 ml of a 1 mol/l solution of potassium hydroxide and stirred for 20 min. at 10–15° C. The solid is filtered, rinsed in suspension with water until a neutral pH, then dried in the drer. 10.3 g of the product sought is thus obtained in the form of a beige powder (yield=78%).

F=174° C.

PREPARATION II

Dimethylcarbamothioic acid, S-[4-[-4-(trifluoromethyl)benzoyl]phenyl] ester 10.3 g (29·10$^{-3}$ mol) of the compound obtained according to preparation I is placed in a flask, under an atmosphere of nitrogen, and the product is held at 250–260° C. for 1 hour. After cooling, approx. 15 ml of ethyl acetate is added, the mixture is brought to a slight reflux, then left to cool down to 0° C. After approx. 10 hours at this temperature, the crystallised solid is filtered and the solid is rinsed with approx. 10 ml of cyclohexane. After drying in the drier, 6.2 g of the product sought is obtained in the form of beige crystals (yield=60%).

F=140° C.

PREPARATION III (4-mercaptophenyl)-[4-(trffluoromethyl)phenyl] methanone

A suspension of 6.1 g (17.3·10$^{-3}$ mol) of the compound obtained according to preparation II is prepared in 65 ml of methanol. After having deoxygenated the medium by bubbling-through with nitrogen, 10 ml (i.e. 34·10$^{-3}$ mol) of a solution of sodium methylate in methanol is added, then the reaction mixture is raised to 40° C. while stirring for three hours. Partial concentration is then carried out (approx. 25 ml of methanol is eliminated) under reduced pressure and the solution is poured into a mixture of ice and diluted hydrochloric acid. The sought product precipitates. The solid product is separated by filtration and washed with water until neutral pH. After drying in the drier, 4.8 g of the product sought is obtained in the form of a clear green solid.

F=150° C.

EXAMPLE 13

[4-[4-(trifluoromethyl)benzoyl]phenyl]1-thio-2,3,4-tri-O-acetyl-α-D-xylopyranoside Operating in a similar manner to example 9, starting from the compound obtained according to preparation III, the sought product is obtained in the form of a beige solid (yield=27%).

F=60° C.

$[\alpha]^{22}_D$=+145° ( c=0.25; $CH_2Cl_2$)

EXAMPLE 14

[4-[4-(trlfluoromethyl)benzoyl]phenyl]1-thio-α-D-xylopyranoside

Operating in a similar manner to example 10, starting from the compound obtained according to example 13, the sought product is obtained in the form of a cream amorphous solid (yield=95%).

F=172° C.

$[\alpha]^{24}_D$=+211° (c=0.35; $CH_3OH$)

EXAMPLE 15

[4-[4-(trifluoromethyl)benzoyl]phenyl]2,3,4tri-O-acetyl-1,5dtioth-α-D-xylopyranoside Operating in a similar manner to example 9, starting from 1,2,3,4-tetra-O-acetyl-5-thio-D-xylose and the compound obtained according to preparation III, the sought product is obtained in the form of a white powder (yield=18%).

F=70° C.

$[\alpha]^{25}_D$=+215° (c=0.45; $CH_2Cl_2$)

EXAMPLE 16

[4-[4-trifluoromethyl)benzoyl]phenyl]1,5-dithio-α-D-xylopyranoside

Operating in a similar manner to example 10, starting from the compound obtained according to example 15, the sought product is obtained in the form of a white powdery solid (yield=84%).

F=104° C.

$[\alpha]^{25}_D$=+399° (c=0.50; DMSO)

PREPARATION IV (4hydroxyphenyl)[4-(methylsulphinyl)phenyl] methanone

A solution of 15 g (61.4·1o$^{-3}$ mol) of (4-hydroxyphenyl) [4-(methylthio)-phenyl]methanone is prepared in 200 ml of methanol. This is cooled down to approx. 5° C. with the aid of an ice bath and 4.12 g (61.4·10$^{-3}$ mol) of 3-chloro-benzenecarboperoxoic acid (mCPBA) is added by fractions titrating 75%. The reaction medium is kept stirring for 15 min. after completion of the addition and hydrolysis is performed on a diluted solution of sodium bicarbonate. Extaction is performed with the aid of ethyl acetate and the phase obtained is washed with water until neutrality, dried and concentrated under reduced pressure. 13.2 g of a white solid composed of the sought product is thus obtained in a mixture with (4-hydroxyphenyl)[4-(methylsulphonyl) phenyl]methanol.

PREPARATION V (4-hydroxyphenyl)[4-(methylsulphonyl)phenyl] methanone

A suspension of 13.2 g of the compound obtained according to preparation IV is prepared in 150 ml of methanol and 11.7 g (50.8·10$^{-3}$ mol) of mCPBA is added by portions while stirring (titrating 75%). The reaction mixture is kept stirring for 30 minutes, then hydrolysis is performed on a cold solution of sodium bicarbonate. Extraction is performed with the aid of ethyl acetate and the organic phase is washed with water until neutrality, dried then concentrated under reduced pressure. 13.6 g of the product sought is thus obtained in the form of a white solid (yield=97%).

F=144° C.

PREPARATION VI

Dimethylcarbamothiolc acid, O-[4-[4-(methylsulphonyl)benzoyl]phenyl]ester

Operating in a similar manner to preparation I, starting from the compound obtained according to preparation V, the sought product is obtained in the form of a beige solid (yield=69%).

F=150° C.

PREPARATION VII

Dimethylcarbamothioic acid, S-[4-[4-(methylsulphonyl)benzoyl]phenyl]ester

Operating in a similar manner to preparation II, starting from the compound obtained according to preparation VI, the sought product is obtained in the form of beige crystals (yield=91%).

F=172° C.

PREPARATION VIII (4mercaptophenyl)[4-(methylsulphonyl)phenyl] methanone

Operating in a similar manner to preparation III, starting from the compound obtained according to preparation VII (adding dimethyl formamide to solubilise the product), the sought product is obtained in the form of a cream solid (yield=95%).

F=176° C.

EXAMPLE 17

[4-[4-(methylsulphonyl)benzoyl]phenyl]2,3,4tri-O-acetyl-1,5-dithio-α-D-xylopyranoside Operating in a similar manner to example 15, starting from the compound obtained according to preparation VIII, the sought product is obtained in the form of a beige solid (yield=31%).

F=86° C.

$[\alpha]^2_D$=+293° (c=0.44; DMSO)

EXAMPLE 18

[4-[4-(methylsulphonyl)benzoyl]phenyl]1,5-dithio-α-D-xylopyranoside

Operating in a similar manner to example 10, starting from the compound obtained according to example 17, the sought product is obtained in the form of a pale yellow solid (yield=90.5%).

F=100° C.

$[\alpha]^{26}_D$=+381° (c=0.58; DMSO)

The antiatheromatous activity of the compounds according to the invention has been demonstrated on female mice, deficient in apolipoprotein E (homozygotes). According to the report on this test, the product to be evaluated is administered in the food (standard diet) for 14 weeks. After this space of time, the mice undergo euthanasia and samples are taken from the heart and the aortic arch. The damaged areas are evaluated according to the method described in Arteriosclerosis, 1990, 10, p. 316–323.

Table I shows the results obtained according to this test carried out with the compound of example 2 at difference doses. The results are expressed in percentage reduction of the area of the atheroma platelets, as compared with a group of untreated control mice.

TABLE 1

| dose administered (mg/kg) | 10 | 100 | 300 |
|---|---|---|---|
| reduction (%) | −32 | −51 | −71 |

By way of comparison, the compound [4-(4-cyanobenzoyl)phenyl]1,5-dithio-β-D-xylopyranoside, previously described in EP-A0290321, was also tested. in the dose of 300 mg/kg, this compound reduces the damaged area by 30%. As shown in table I, the same biological result is achieved with only 10 mg/kg of the compound according to example 2. This demonstrates the superiority of the compound of the invention in this activity when the anomeric carbon of the xylose is in the a configuration.

During the 14 weeks of the test described above, aimed at evaluating the antiatheromatous properties of the compounds, the serum cholesterol rate of the treated mice and the control mice was measured, and the result is expressed in the form area-under-curve (AUC) of cholesterol during the whole duration of the test. The results obtained with the compound of example 2 are entered in table II where AUC represents the area-under-curve (expressed in g.day.$1^{-1}$) and the variation (in percentage) is evaluated by reference to the control group.

TABLE II

| dose (mg/kg) (Ex 2) | 0 (control) | 10 | 100 | 300 |
|---|---|---|---|---|
| AUC | 583 ± 23 | 585 ± 15 | 507 ± 16 | 505 ± 20 |
| variation (%) | — | 0 | −13 | −13 |

The analysis of the values observed reveals a hypocholesterolemiant effect which only appears over the period of 14 weeks with the 100 mg/kg dose whereas the antiatheromatous effect is significant from the 10 mg/kg dose.

However, in view of the probability of a correlation between the antiatheromatous activity observed and a capacity of the compound to lower the serum cholesterol rate, and in order to obtain a screening result as quickly as possible, the compounds according to the invention were evaluated according to their potential for diminishing the cholesterolaemia of mice subjected to a diet rich in fats. The test was performed by administration to female mice of strain C57BL/6J. The report is as follows: on the first day (J0), the mice undergo fasting from the 9.00 to 17.00 hours, a blood sample being taken at 14.00 hours. At 17.00 hours, a determined amount of food (fatty diet containing 1.25% of cholesterol and 0.5% of cholic acid) is distributed. On the second day (J1), at 9.00 hours, the remains of the food are weighed and the mice undergo fasting from 9.00 to 14.00 hours. At 14.00 hours, a blood sample is taken. For the groups of treated mice, the compound is administered by tubing, in suspension in a solution of gummy water, at 3%, on the second day (J1) at 9.00 hours. The control groups only receive the gummy water.

The compounds were tested at the dose of 100 mg/kg. The serum total cholesterol is analysed and the results are expressed in percentage inhibition of the increase in cholesterolaemia as compared with the control group. The results obtained are entered in the column "Activty" of table III. Moreover, it can be seen that the analysis of the cholesterol content of the various classes of serum lipoproteins reveals a favourable effect of the product on the HDL-cholesterol/total cholesterol ratio.

The products with formula I according to the invention can be administered, preferably orally, in the form of tablets or capsules, each containing 20 to 500 mg of a compound with formula I as the active principle, in association with excipients. The posology will be about 1 to 4 doses per day. These products will be prescribed for the prevention or treatment of atheromatous risk.

TABLE III

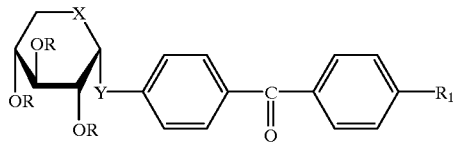

| Ex | $R_1$ | X | Y | R | Activity (%) |
|---|---|---|---|---|---|
| 1 | CN | S | S | Ac | −40 |
| 2 | CN | S | S | H | −38 |
| 3 | CN | O | O | Ac | −46 |
| 4 | CN | O | O | H | −39 |
| 5 | CN | O | S | Ac | −41 |
| 6 | CN | O | S | H | −38 |
| 7 | CN | S | O | Ac | −26 |
| 8 | CN | S | O | H | −12 |
| 9 | $CF_3$ | O | O | Ac | — |
| 10 | $CF_3$ | O | O | H | −5 |
| 11 | $CF_3$ | S | O | Ac | −23 |
| 12 | $CF_3$ | S | O | H | −7 |
| 13 | $CF_3$ | O | S | Ac | −24 |
| 14 | $CF_3$ | O | S | H | −26 |
| 15 | $CF_3$ | S | S | Ac | −17 |
| 16 | $CF_3$ | S | S | H | −19 |
| 17 | $SO_2CH_3$ | S | S | Ac | −36 |
| 18 | $SO_2CH_3$ | S | S | H | — |

What is claimed is:

1. A substantially pure α-D-xylose compound of the formula I:

(I)

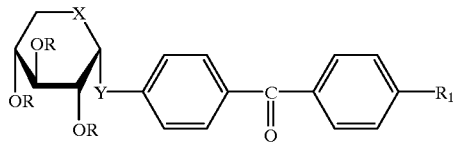

wherein
X and Y represent, independently of one another, an oxygen atom or a sulphur atom,
$R_1$ represents a CN, $CF_3$ or $SO_2CH_3$ group, and
R represents a hydrogen atom or an aliphatic acyl group containing 2 to 5 carbon atoms.

2. A substantially pure α-D-xylose compound of the formula I according to claim 1, in which $R_1$ is CN.

3. A substantially pure α-D-xylose compound of the formula I according to claim 1, in which X=Y=S and $R_1$ is CN.

4. A substantially pure α-D-xylose compound of the formula I according to claim 1, in which X=Y=O and $R_1$ is CN.

5. A method for preparing α-D-xylose compound according to claim 1, comprising:
reacting a benzophenone compound of the formula II:

(II)

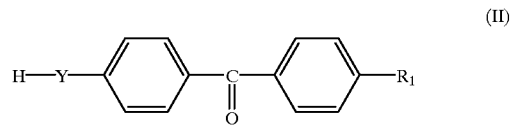

with a D-xylose compound of the formula III:

(III)

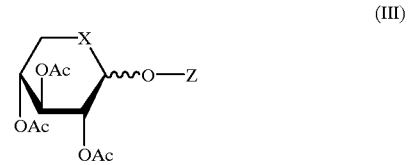

wherein Y, $R_1$ and X are defined above,
Ac represents an acetyl group and Z represents an acetyl group or a trichloromethylimino group,
the reaction being conducted in a solvent and in the presence of a Lewis acid which is boron trifluoride etherate.

6. A pharmaceutical composition for treatment of atheroma, comprising a therapeutically effective quantity of at least one compound of the formula I according to claim 1 and a physiologically acceptable excipient.

7. A method for treating atherosclerosis comprising administering an effective amount of a composition according to claim 6.

8. A method for preparing a substantially pure α-D-xylose compound according to claim 5, wherein R is an acetyl group, further comprising reacting said compound with a base to thereby replace the acetyl group with a hydrogen atom and to obtain the compound of the formula I in which R is a hydrogen atom.

9. A method for preparing a substantially pure α-D-xylose compound according to claim 8, comprising reacting said compound in which R is a hydrogen atom with a $C_2$–$C_5$ acid chloride or an anhydride of a $C_2$–$C_5$ aliphatic acid in the presence of an aprotic base and in a solvent, to thereby obtain the compound of the formula I in which R is an acyl group.

* * * * *

UNITED STATES PATENT AND TRADEMARK OFFICE
CERTIFICATE OF CORRECTION

PATENT NO. : 6,291,433 B1
DATED : September 18, 2001
INVENTOR(S) : Veronique Barberousse, Christiane Legendre, Soth Samreth and Alan Dunlap Edgar It is certified that error appears in the above-identified patent and that said Letters Patent is hereby corrected as shown below:

<u>Title page,</u>
Item [22], PCT Filed: change "July 7, 1999" to -- June 11, 1999 --.

Signed and Sealed this

Twenty-third Day of July, 2002

Attest:

JAMES E. ROGAN
*Attesting Officer*   *Director of the United States Patent and Trademark Office*